US012595491B2

(12) United States Patent
Itoh et al.

(10) Patent No.: US 12,595,491 B2
(45) Date of Patent: Apr. 7, 2026

(54) COMPOUND INTRODUCTION APPARATUS AND COMPOUND INTRODUCTION METHOD

(71) Applicant: CANON KABUSHIKI KAISHA, Tokyo (JP)

(72) Inventors: Yoshinori Itoh, Kanagawa (JP); Tatsuaki Orihara, Tokyo (JP); Shinichi Sakurada, Tokyo (JP); Tsutomu Shiratori, Tokyo (JP); Sachiko Yamauchi, Kanagawa (JP); Nobuyuki Kuwabara, Tokyo (JP); Futoshi Hirose, Kanagawa (JP); Takeshi Okada, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 1060 days.

(21) Appl. No.: 17/693,829

(22) Filed: Mar. 14, 2022

(65) Prior Publication Data

US 2022/0298529 A1 Sep. 22, 2022

(30) Foreign Application Priority Data

Mar. 18, 2021 (JP) ................................. 2021-044715
Mar. 10, 2022 (JP) ................................. 2022-037270

(51) Int. Cl.
B01L 3/00 (2006.01)
B01L 1/00 (2006.01)
(Continued)

(52) U.S. Cl.
CPC ............... C12N 15/87 (2013.01); B01L 3/56 (2013.01); B01L 7/00 (2013.01);
(Continued)

(58) Field of Classification Search
CPC ................. B01L 2400/0605; B01L 2200/0647
See application file for complete search history.

(56) References Cited

U.S. PATENT DOCUMENTS

2005/0217741 A1* 10/2005 Bohm .................. G05D 7/0694
137/828
2006/0028908 A1* 2/2006 Suriadi ............... F16K 99/0057
366/146
(Continued)

FOREIGN PATENT DOCUMENTS

WO 2008/153968 A2 12/2008

OTHER PUBLICATIONS

Aleli Campbell et al., "Thermal Bioprinting Causes Ample Alterations of Expression of LUCAT1, IL6, CCL26, and NRN1L Genes and Massive Phosphorylation of Critical Oncogenic Drug Resistance Pathways in Breast Cancer Cells," 8 (Art. 82) Frontiers in Bioeng. Biotech. 1-15 (Feb. 2020).
(Continued)

*Primary Examiner* — Nathan A Bowers
(74) *Attorney, Agent, or Firm* — Venable LLP

(57) ABSTRACT

Provided is a compound introduction apparatus including: a processing chamber; a first heater that introduces an introduction-target compound into a cell inside the processing chamber; a supply flow channel for supplying a cell suspension containing the cell and the introduction-target compound to the processing chamber; a discharge flow channel for discharging the cell suspension from the processing chamber; a second heater that prevents backflow of the cell suspension from the processing chamber into the supply flow channel; and a third heater that pressurizes the discharge flow channel.

15 Claims, 10 Drawing Sheets

(51) Int. Cl.
  *B01L 7/00*          (2006.01)
  *C12N 15/87*        (2006.01)

(52) U.S. Cl.
  CPC ...  *B01L 2200/0647* (2013.01); *B01L 2300/18*
                (2013.01); *B01L 2400/0605* (2013.01)

(56)              References Cited

U.S. PATENT DOCUMENTS

| | | | | |
|---|---|---|---|---|
| 2006/0051214 | A1* | 3/2006 | Ussing .................... | B01F 33/05 |
| | | | | 417/51 |
| 2006/0238573 | A1* | 10/2006 | Hu ......................... | B41J 2/1643 |
| | | | | 29/25.35 |
| 2009/0046128 | A1* | 2/2009 | Giri ...................... | B01L 3/0268 |
| | | | | 347/56 |
| 2014/0307032 | A1* | 10/2014 | Xie ...................... | B41J 2/14064 |
| | | | | 347/54 |
| 2019/0366340 | A1* | 12/2019 | Govyadinov ....... | F16K 99/0019 |
| 2021/0245153 | A1* | 8/2021 | Kornilovich ........ | B01L 3/50273 |

OTHER PUBLICATIONS

Hirose et al., U.S. Appl. No. 17/693,854, filed Mar. 14, 2022.
Sakurada et al., U.S. Appl. No. 17/693,836, filed Mar. 14, 2022.
Yamauchi et al., U.S. Appl. No. 17/693,844, filed Mar. 14, 2022.

* cited by examiner

COMPOUND INTRODUCTION APPARATUS AND COMPOUND INTRODUCTION METHOD

BACKGROUND OF THE INVENTION

Field of the Invention

The present invention relates to a technique for introducing a compound into a cell.

Description of the Related Art

Techniques for introducing a compound including a gene into a cell have been known. The introduction method includes a chemical or biological introduction method using a cationic substance or a virus on a living cell. Also, various methods have been developed including physical introduction methods such as an electroporation method and a gene gun method, which are expected to be low in toxicity, and a microinjection method, with which a wide range of compounds to be introduced are selectable and introduction is reliable.

In recent years, cell therapeutic drugs and induced pluripotent stem cells, in which genes are into cells to modify the cells' properties, have emerged, and there has been a demand for a method of introducing a compound into cells for direct administration into the human body. An introduction method with high biological safety has therefore been required.

The description of International Publication No. WO2008/153968 (hereinafter Document 1) discloses a technique for introducing an introduction-target compound into cells by using an inkjet device used as an image printing apparatus. In Document 1, the introduction-target compound is introduced into cells by causing the cells to flow through a micro-sized flow channel, so that a shear force is generated by their interaction with the wall surface of the flow channel. Moreover, as methods of causing that shear force action, a thermal inkjet method utilizing bubble generation of a solvent, a piezoelectric inkjet method utilizing deformation of a piezoelectric element are exemplarily shown.

The technique of Document 1 is an introduction method with high biological safety since it does not use a special virus, a cationic substance, or the like.

SUMMARY OF THE INVENTION

A compound introduction apparatus according to an aspect of the present invention is a compound introduction apparatus for introducing a compound into a cell, including: a processing chamber; an introduction unit configured to introduce the compound into the cell inside the processing chamber; a supply flow channel for supplying a cell suspension containing the cell and the compound to the processing chamber; a discharge flow channel for discharging the cell suspension from the processing chamber; a backflow preventing unit configured to prevent backflow of the cell suspension from the processing chamber into the supply flow channel; and a pressurization unit configured to pressurize the discharge flow channel.

Further features of the present invention will become apparent from the following description of exemplary embodiments with reference to the attached drawings.

DESCRIPTION OF THE EMBODIMENTS

From the present inventors' consideration, it has been found that the technique of Document 1 does not sufficiently improve the compound introduction efficiency.

As a result, the present inventors have made vigorous consideration to provide a compound introduction apparatus capable of improving the compound introduction efficiency while ensuring the biological safety, and have arrived at the present invention.

Embodiments according to the present invention will be described below with reference to the drawings. Note that the following embodiments do not limit the present invention, and not all the combinations of the features described in these embodiments are necessarily essential. Incidentally, the same components will be described with the same reference sign given thereto.

First Embodiment

<Compound Introduction Apparatus>

Figure 1:
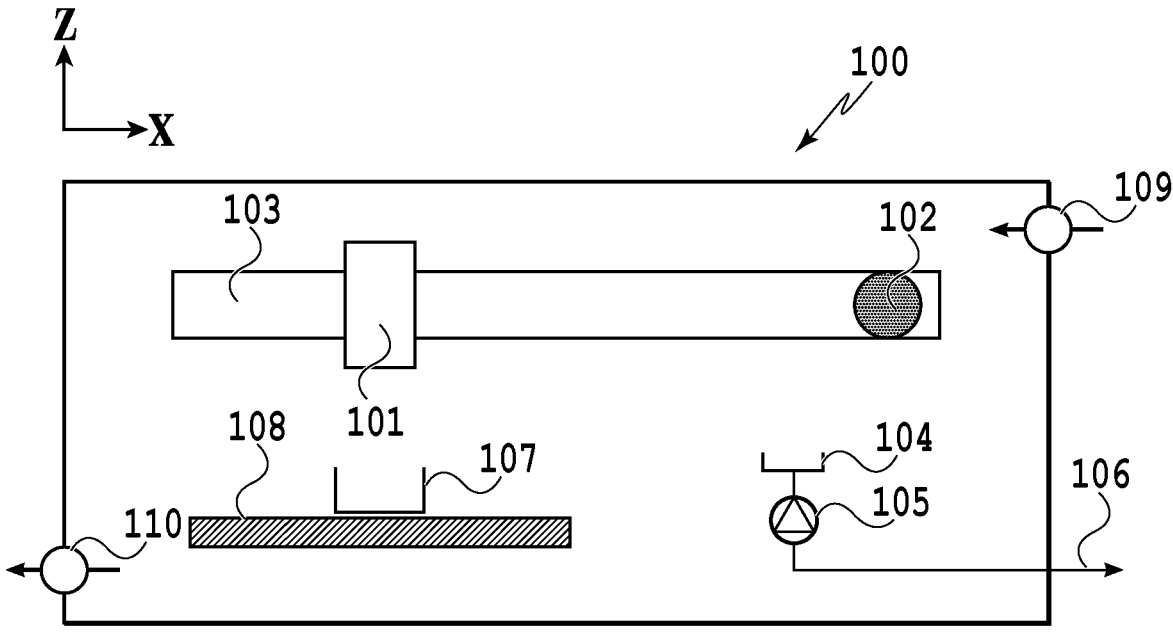
FIG. 1 is a diagram illustrating one example of a compound introduction apparatus.

FIG. 1 is a diagram illustrating one example of a compound introduction apparatus 100 in the present embodiment. The compound introduction apparatus 100 in the present embodiment is an apparatus including an inkjet-type ejection head 101. The ejection head 101 is filled with a liquid containing a compound and cells into which the compound is to be introduced. Herein, this liquid will be referred to as "cell suspension" (also called "cell-containing liquid"). The ejection head 101 may be called "cell processing head" or "liquid ejection head". The cell suspension after being ejected from the ejection head 101 contains cells into which the compound has been introduced. The compound introduction apparatus 100 as above may be called "ejection apparatus" or "cell processing apparatus". Also, the compound to be introduced into cells may be called "introduction-target compound". A configuration of the compound introduction apparatus 100 will be described below.

FIG. 1 is a diagram schematically illustrating the compound introduction apparatus 100 in the present embodiment. The compound introduction apparatus 100 illustrated in FIG. 1 includes a driving motor 102, a driving belt 103 connected to the driving motor 102, and the ejection head 101 to be conveyed by the driving belt 103. The ejection head 101 can be moved to any position within a region within which the ejection head 101 can be conveyed, by driving the driving motor 102.

The liquid filled in the ejection head 101 is filled into flow channels and ejection ports in the ejection head 101 by bringing the ejection head 101 into contact with a suction mechanism 104 and actuating a suction motor 105. Also, in a case where ejection has not been performed for a certain period of time, the liquid inside the ejection head 101 can be discharged by bringing the ejection head 101 into contact with the suction mechanism 104 and actuating the suction motor 105. The liquid resulting from the suction and the discharge is discharged to the outside of the apparatus through a waste liquid tube 106.

The cells with the compound introduced therein are ejected from the ejection head 101 toward a culture dish 107 fixed to the top of a processing stage 108. The cells with the compound introduced therein can be obtained in this manner.

Mist and dust inside the apparatus can be reduced by an air suction port 109 having a fan and a filter and an air discharge port 110. This makes it possible to introduce the compound while also reducing contamination.

<Configuration of Ejection Head>

Figure 2:
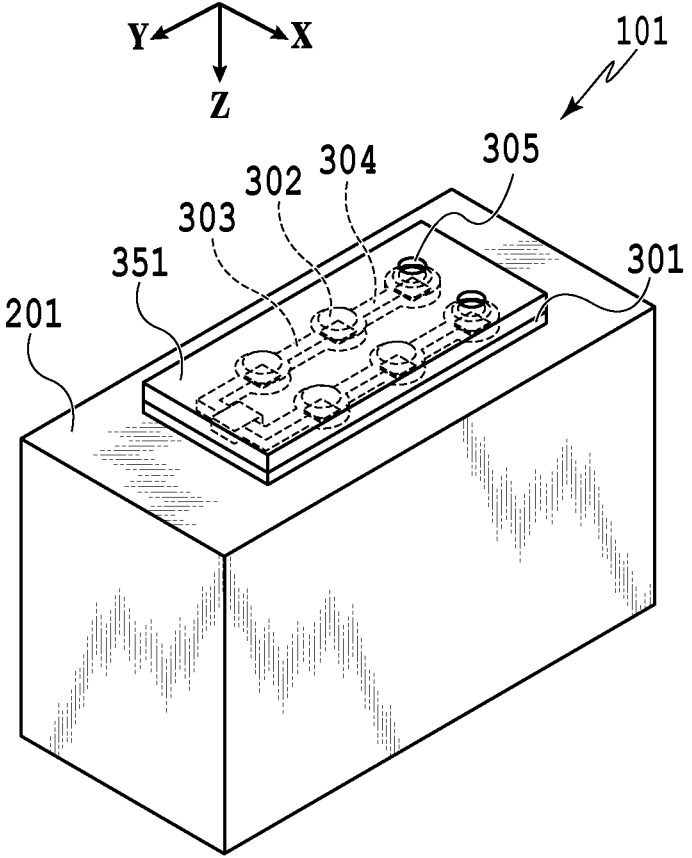
FIG. 2 is a perspective view of an ejection head.

FIG. 2 is a perspective view of the ejection head 101 in the present embodiment. The ejection head 101 includes a reservoir part 201 which holds therein the cell suspension containing the compound and cells into which the compound is to be introduced, and processing chambers 302 in which processing to form holes in the surface membranes of the cells is performed to introduce the compound into the cells. The ejection head 101 includes supply flow channels 303 for supplying the cell suspension from the reservoir part 201 to the respective processing chambers 302, and discharge flow channels 304 for discharging the cell suspension from the respective processing chambers 302 to ejection ports 305. The ejection head 101 also includes the ejection ports 305 for ejecting the cells with the compound introduced therein from the ejection head to the outside. Note that each processing chamber 302 may be called "introduction chamber". Each supply flow channel 303 is a flow channel upstream of the corresponding processing chamber 302. Each discharge flow channel 304 is a flow channel downstream of the corresponding processing chamber 302. Each ejection port 305 is formed at a portion of the corresponding discharge flow channel 304. In the present embodiment, the reservoir part 201 is made of a resin, and an electronic substrate 301 made of silicon is mounted to the bottom of the reservoir part 201.

Figure 3A:
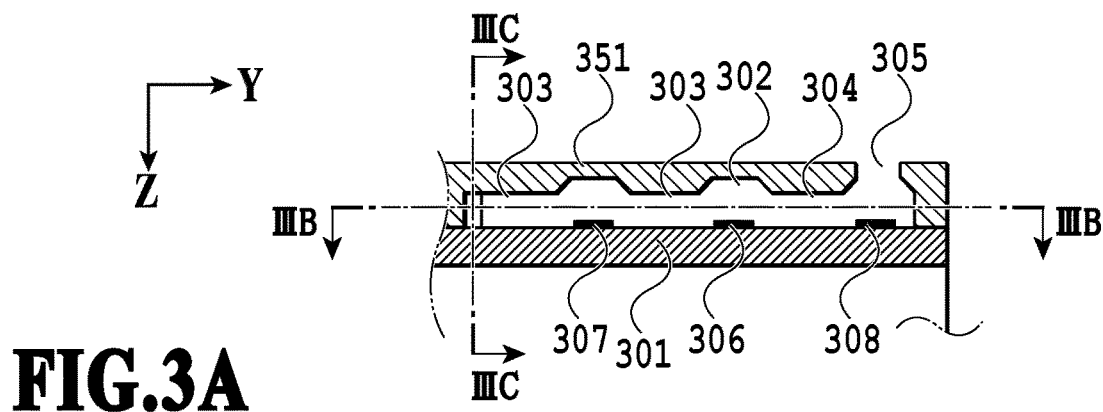
FIGS. 3A to 3C are views illustrating an example of the positional relationship among components formed on an electronic substrate.
Figure 3B:
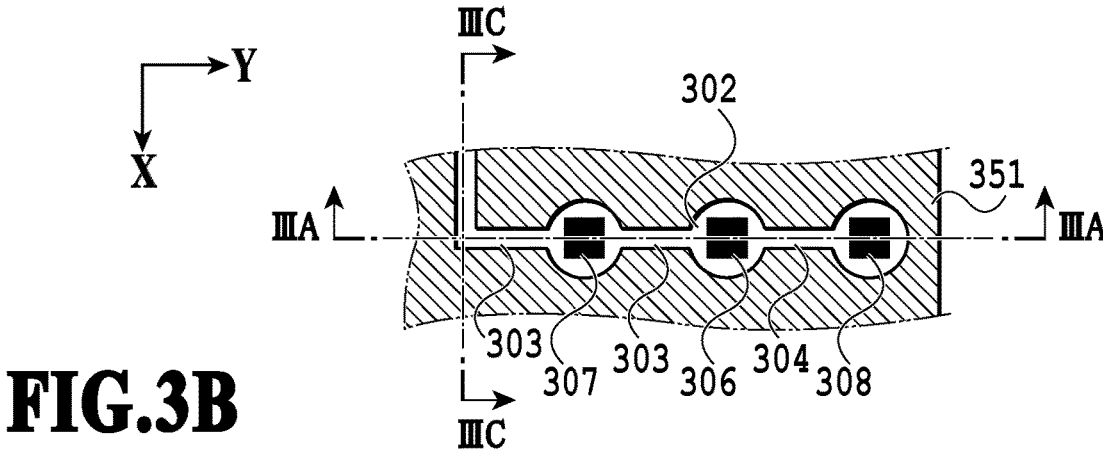
Figure 3C:
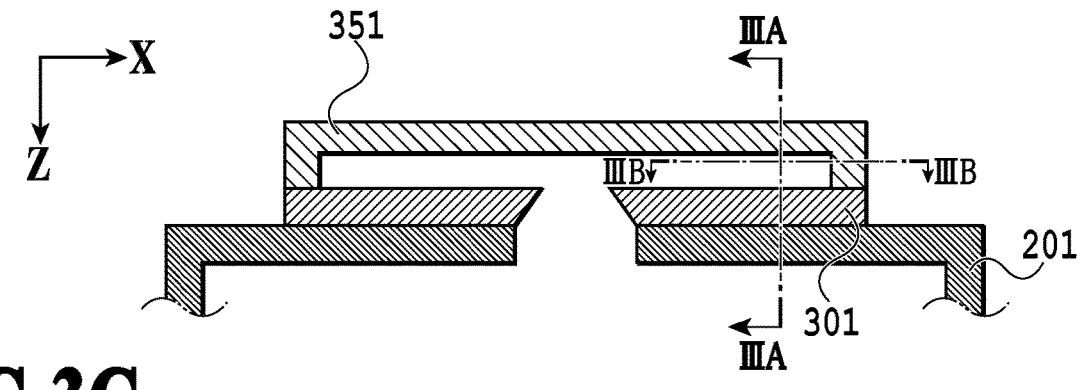

FIGS. 3A to 3C are views illustrating an example of the positional relationship among components formed on the electronic substrate 301. FIG. 3A is a vertical cross-sectional view along line IIIa in FIGS. 3B and 3C. FIG. 3B is a horizontal cross-sectional view along line IIIb in FIGS. 3A and 3C. FIG. 3C is a vertical cross-sectional view along line IIIc in FIGS. 3A and 3B. Note that the description will be given on the assumption that, in FIGS. 3A and 3C, the −Z direction is a direction toward the top of the sheet.

A flow channel forming member 351 is formed on the electronic substrate 301. The flow channel forming member 351 is made of a resin material, such as polypropylene, for example. The processing chambers 302 and various flow channels are formed between the electronic substrate 301 and the flow channel forming member 351. The ejection ports 305 are formed in the flow channel forming member 351. The supply flow channels 303, the processing chambers 302, and the discharge flow channels 304 are formed between the electronic substrate 301 and the flow channel forming member 351. Note that, in the present embodiment, a photo-curable resin for use in manufacturing commonly known print heads for inkjet printing is used for the supply flow channels 303, the processing chambers 302, the discharge flow channels 304, and the ejection ports 305 formed on the electronic substrate 301. However, the material is not limited to this example, and the flow channel forming member 351 may be made of a metal, glass, or the like, for instance.

The compound introduction apparatus 100 in the present embodiment can introduce the compound into cells by instantaneously applying at least mechanical energy to energy generation elements. As a method that enables instantaneous energy application as above, a piezoelectric inkjet method can be used in which a piezoelectric element is disposed in a micro flow channel and exhibits a mechanical action by using its displacement caused via voltage application. Alternatively, a thermal inkjet method can be used in which a heater (heating element) having high electrical resistance is disposed in a flow channel, and the heater is caused to generate heat via voltage application to thereby generate a bubble on the order of microseconds in a liquid near the heater to exhibit a mechanical action and a thermal action.

In each processing chamber 302 on the electronic substrate 301 in the present embodiment, a first heater 306, which is an energy generation element, is arranged. Second heaters 307 and third heaters 308, which are energy generation elements, are also arranged on the electronic substrate 301. Besides the first heaters 306, the second heaters 307, and the third heaters 308, a driving control unit (not illustrated) and power wirings (not illustrated) for driving the heaters are disposed in the electronic substrate 301.

The first heater 306 in each processing chamber 302 is capable of generating heat via voltage application to thereby boil the liquid (cell suspension) near it and generate a bubble therein on the order of microseconds. This makes it possible to apply a mechanical action and a thermal action to the cell in the processing chamber 302. Each second heater 307 is a backflow preventing unit configured to prevent backflow of the cell suspension from inside the processing chamber 302 into the supply flow channel 303. Each third heater 308 is a pressurization unit configured to apply a pressure to the discharge flow channel 304.

In the present embodiment, an example has been shown in which heaters are used as the first heater 306, which is an introduction unit configured to introduce the introduction-target compound into the cell in the processing chamber 302, the second heater 307, which is a backflow preventing unit, and the third heater 308, which is a pressurization unit. However, the present embodiment is not limited to this configuration, and any energy generation elements that generate energy may be used. For example, a pressurization unit using a piezoelectric element or a pressurization unit using an electrostatic actuator may be used as the energy generation element. That is, any energy generation elements can be used as the introduction unit arranged in the processing chamber, the backflow preventing unit arranged in the supply flow channel, and the pressurization unit arranged in the discharge flow channel. Also, the same type of energy generation element may be used as these units or different types of energy generation elements may be used as some of the units.

The present embodiment will be described based on the example in where a heater is used as each unit. Also, the third heater 308, which is a pressurization unit, also serves as a driving source for discharging the cell suspension from the ejection port 305.

<Method of Controlling Compound Introduction Apparatus>

Next, a method of controlling the compound introduction apparatus 100 in the present embodiment will be described. The control method to be described below is performed by control by a CPU 505 in the control system in FIG. 5 to be described later.

Firstly, the cell suspension is filled into the reservoir part 201 of the ejection head 101, each supply flow channel 303, each processing chamber 302, each discharge flow channel 304, and the vicinity of each ejection port 305. For example, the cell suspension held in the reservoir part 201 can be filled into the supply flow channel 303, the processing chamber 302, the discharge flow channel 304, and the vicinity of the ejection port 305 by suction with a mechanism like the suction mechanism 104 in FIG. 1. Alternatively, the ejection head 101 filled with the cell suspension in advance may be attached to the compound introduction apparatus 100. Incidentally, the suction mechanism 104 can also be used as a cap to prevent the head from becoming dry while no introduction process is performed.

Next, electric power is supplied to the second heater 307, which is a backflow preventing unit, and the third heater 308, which is a pressurization unit, thus boiling and vaporizing the liquid, such as water, contained in the cell suspension inside the respective flow channels, each of which is of a micron size.

Figure 4:
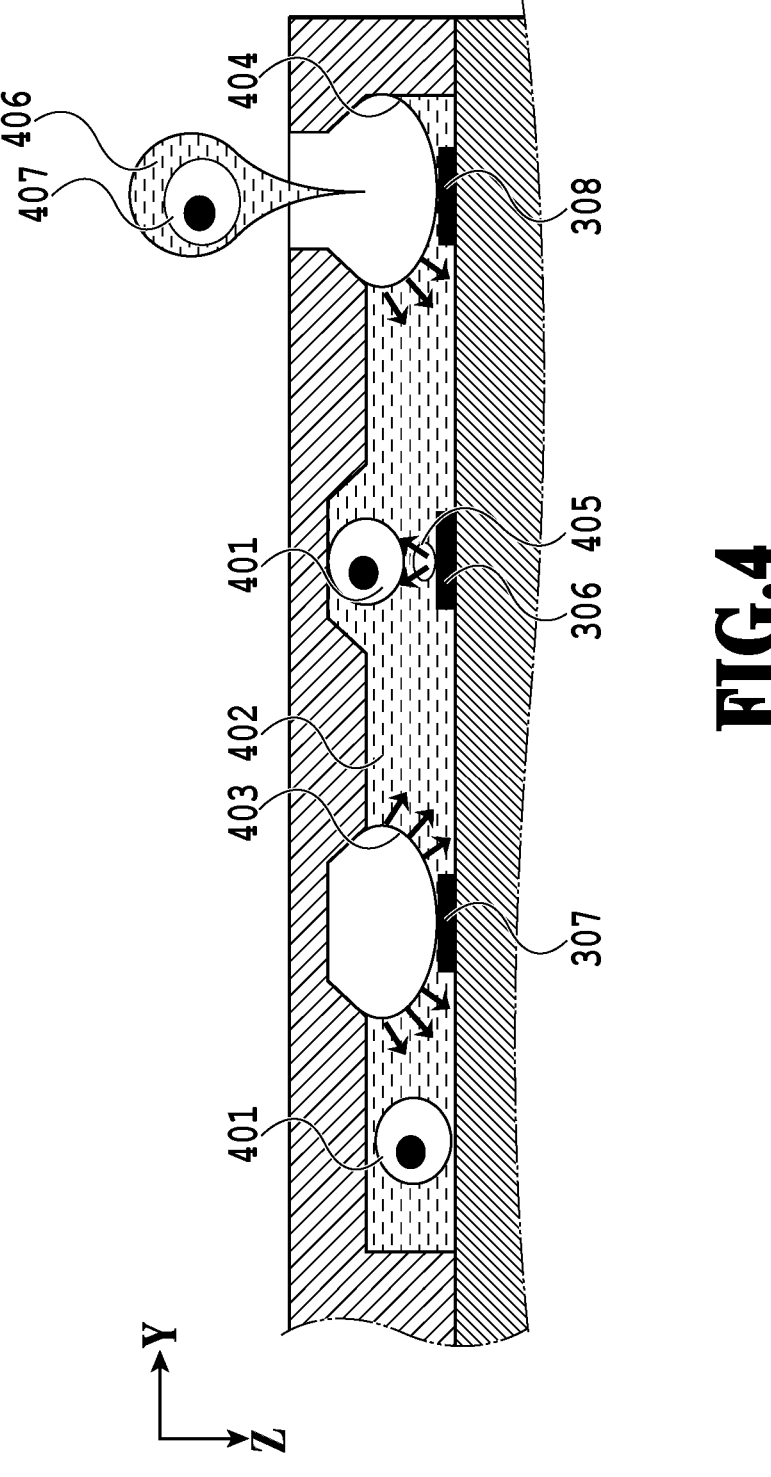
FIG. 4 is a view schematically illustrating a state of a cell suspension in flow channels in the ejection head.

FIG. 4 is a view schematically illustrating a state of the cell suspension in flow channels in the ejection head 101 over the cross-sectional view illustrated in FIG. 3A. A bubble 403 generated by the second heater 307, which is a backflow preventing unit, and a bubble 404 generated by the third heater 308, which is a pressurization unit, prevent flow of the cell suspension. In other words, the bubbles create a state where the cell suspension is temporarily trapped in and around the processing chamber 302. Note that, in the present embodiment, electric power is simultaneously supplied to the second heater 307, which is a backflow preventing unit, and the third heater 308, which is a pressurization unit. While the example in which the supply flow channel 303 and the discharge flow channel 304 are simultaneously pressurized as above to create the state where the cell suspension is temporarily trapped in the processing chamber 302 will be described, the supply flow channel 303 and the discharge flow channel 304 do not necessarily have to be simultaneously pressurized. Electric power may be applied initially to the heater in one of the supply flow channel 303 or the discharge flow channel 304 and, while the pressure in this flow channel is positive relative to the state before the application, electric power may be applied to the heater in the other flow channel. The first heater 306, which is an introduction unit, is not driven before the state of preventing flow of the cell suspension is created.

Note that the time for which electric power is supplied to the second heater 307 and the third heater 308 and the voltage of the electric power are controlled to create a state where film boiling occurs. This is for the second heater 307, which is a backflow preventing unit, and the third heater 308, which is a pressurization unit, to create the state of temporarily trapping the cell suspension in the processing chamber 302. Specifically, in order that the supply flow channel 303 and the discharge flow channel 304 can be temporarily blocked by bubbles in the boiled liquid, it is preferable to generate bubbles of such sizes that fills the diameters of the flow channels. For this reason, the time for which electric power is supplied to the second heater 307 and the third heater 308 and the voltage of the electric power are controlled to create a state of generating a film boiling bubble.

Next, while the pressure in the supply flow channel 303 and the discharge flow channel 304 is positive relative to the state before the start of the pressurization, electric power is supplied to the first heater 306 in the processing chamber 302, which is an introduction unit, to thereby generate a bubble 405 inside the processing chamber 302. More preferably, electric power is supplied to the first heater 306 while the pressure in the supply flow channel 303 and the pressure in the discharge flow channel 304 are substantially in equilibrium and thus preventing flow of the cell suspension in the processing chamber 302. The time for which flow of the cell suspension in the processing chamber 302 is prevented is long in a case where the flow channel diameter of the supply flow channel 303 or the discharge flow channel 304 is small, and is short in a case where the flow channel diameter is large. It is preferable to set the flow channel diameter of each flow channel as appropriate according to the size of the cells to be handled with the above fact taken into account within such a range that a cell can flow through the flow channel without closing it.

Here, it is preferable that the second heater 307, which is a backflow preventing unit, and the third heater 308, which is a pressurization unit, shift to a film boiling state as described above in order to form bubbles that temporarily close the flow channels. On the other hand, the first heater 306, which is arranged in the processing chamber 302, is driven to apply a stress to the surface membrane of a cell 401. For this reason, the first heater 306 does not need to shift to a film boiling state when it is driven. The tension of the cell membrane or the strength of the cell membrane can variously change depending on the cell type or the osmotic pressure of the cell suspension. For this reason, a preferable bubble form varies depending on the state of the cells. Generally, in a case where the strength of the cell membrane is low or the osmotic pressure of the liquid is low, the amount of electric power to be supplied to the first heater 306 in the processing chamber 302 is set to be smaller than the amount of electric power to be supplied to the second heater 307 and the third heater 308. Thus, in some cases, it is advantageous to heat the first heater 306 relatively weakly to shift it to a nucleate boiling state. It is preferable to set the amount of electric power to be supplied to the first heater 306 according to the state of the cells with the above fact taken into account. Note that electric power may be supplied to the first heater 306 according to the state of the cells such that the first heater 306 shifts to a film boiling state when driven.

In order to introduce the introduction-target compound into a cell with high probability, processing to form a hole in the surface membrane of the cell which is necessary for introducing the compound into the cell is performed inside the micro-sized flow channels or the processing chamber 302. Moreover, it is required to subject the cell to a stress of a level that is sufficient but does not rupture the cell, and also to reduce the variation of the effect of the stress to such an extent that cells can be reproducibly and stably processed.

In the present embodiment, the second heater 307, which is a backflow preventing unit, and the third heater 308, which is a pressurization unit, temporarily close the flow channels. This limits flow of cells and brings about a state where a cell is temporarily trapped in the processing chamber 302, which is a micro-sized space. While the cell is trapped in the processing chamber 302, the first heater 306 in the processing chamber is driven. In this way, it is possible to apply a stress to the cell while reducing the stress variation. Also, since a stress generated by a heater is applied directly to the cell, the stress can be applied to a limited region of the cell membrane. This makes it possible to achieve a state of preventing rupture of the cell while applying a stress necessary and sufficient to introduce the compound into the cell. Accordingly, it is possible to improve the compound introduction efficiency while ensuring the biological safety. Specifically, it is possible to achieve high introduction efficiency of the introduction-target compound and a low cell death rate while guaranteeing biological safety.

Note that FIGS. 3A to 3C illustrate an example in which a single processing chamber 302 is disposed between the supply flow channel 303 and the discharge flow channel 304, but the present embodiment is not limited to this example. A plurality of processing chambers may be disposed at positions between the supply flow channel 303 and the discharge flow channel 304. Also, a plurality of sets of a supply flow channel 303, a processing chamber(s) 302, a discharge flow channel 304, and an ejection port 305 may be connected in series. Also, FIGS. 2 and 3A to 3C illustrate an example where a supply port for supplying the cell suspension from the reservoir part 201 to the ejection head 101 separates into two flow channels, and the flow channels are formed in parallel to each other. However, the present embodiment is not limited to this example. The cell suspension may be supplied to a single flow channel from the supply port for supplying the cell suspension from the reservoir part 201 to the ejection head 101. Also, one of the flow channels may be branched off at an intermediate portion and form a plurality of sets of a supply flow channel 303, a processing chamber(s) 302, a discharge flow channel 304, and an ejection port 305 in parallel to each other.

Also, in the above embodiment, an example has been described in which the first heater 306, which is an introduction unit, is not driven before the state of preventing flow of the cell suspension is created, but the embodiment is not limited to this example. For example, in the case of the configuration where the second heater 307, which is a backflow preventing unit, and the third heater 308, which is a pressurization unit, are not driven simultaneously, driving one of the heaters can at least prevent flow on one side. For this reason, the driving of the first heater 306, which is an introduction unit, may be started after at least one of the second heater 307, which is a backflow preventing unit, or the third heater 308, which is a pressurization unit, is driven.

Also, in the present embodiment, an example has been shown in which the diameter of the processing chamber 302 is larger than that of the supply flow channel 303 and the discharge flow channel 304. However, the processing chamber 302 only needs to have such a diameter that a cell does not get stuck therein. In a case where the supply flow channel 303 and the discharge flow channel 304 have such a size that a cell does not get stuck therein, the diameter of the processing chamber 302 may be as large as that of the supply flow channel 303 and the discharge flow channel 304. This applies also to the bubble generation chambers in which the second heater 307 and the third heater 308 are arranged.

Also, in the present embodiment, an example will be described in which the object of interest to be introduced is introduced into a cell mainly by driving the first heater 306. However, the object of interest to be introduced may be introduced into a cell as a result of driving the second heater 307 and the third heater 308. That is, the object of interest to be introduced may be introduced into a cell by stresses generated by the second heater 307 and the third heater 308.

<Control Block Diagram>

Figure 5:
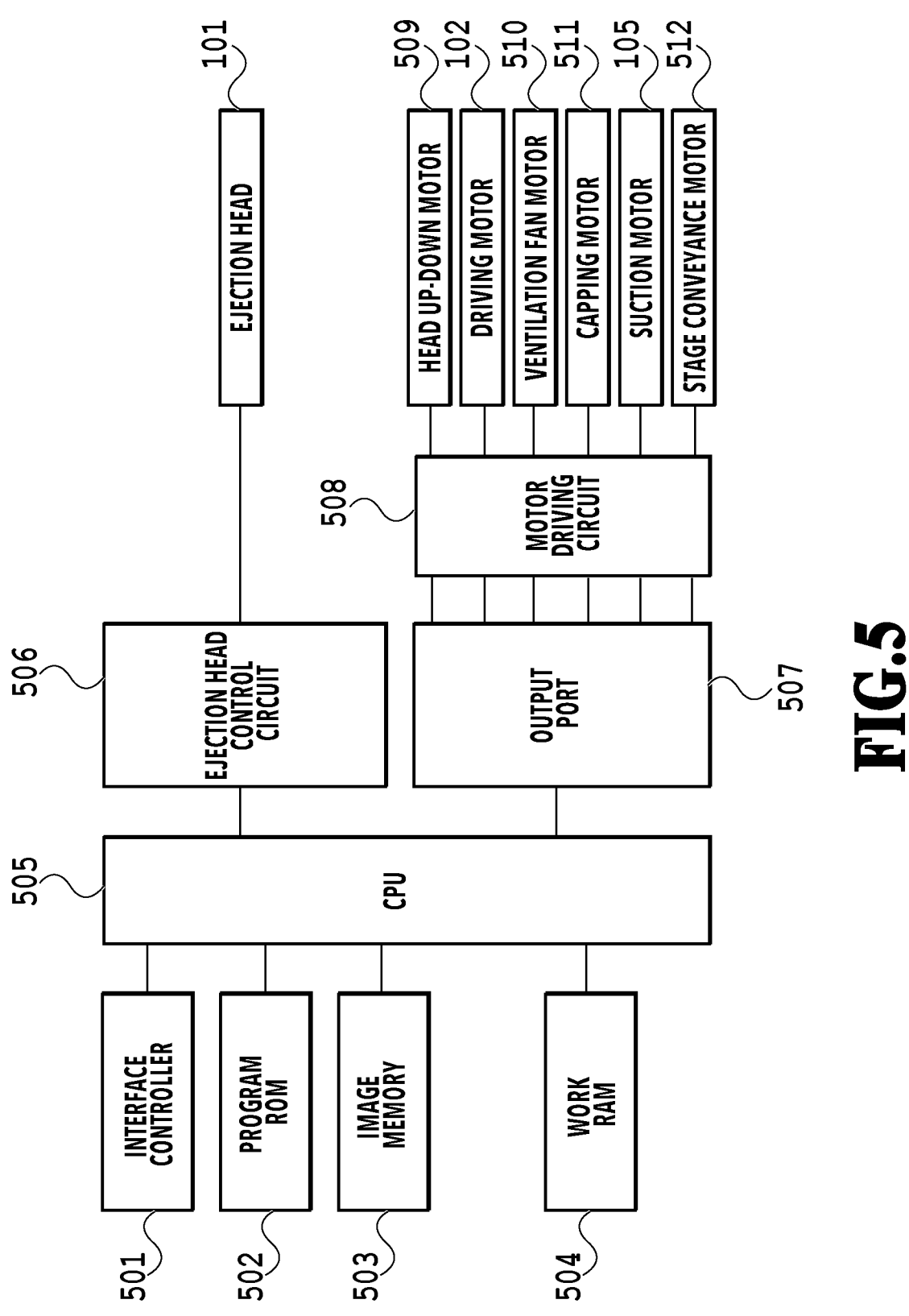
FIG. 5 is a diagram illustrating one example of blocks in a control system of the compound introduction apparatus.

FIG. 5 is a diagram illustrating one example of blocks in the control system of the compound introduction apparatus 100 in the present embodiment. The compound introduction apparatus 100 has the CPU 505, an interface controller 501, a program ROM 502, an image memory 503, a work RAM 504, an ejection head control circuit 506, an output port 507, and a motor driving circuit 508. The present embodiment will be described on the assumption that the compound introduction apparatus 100 controls introduction of any of various compounds in response to an instruction from a host apparatus, such as an external apparatus. However, the present embodiment is not limited to this case. The compound introduction apparatus 100 may be provided with an operation unit or the like and control introduction of any of various compounds in response to an instruction corresponding to an operation on the operation unit.

Output data and a command are sent to the compound introduction apparatus 100 from a host information terminal (e.g., a personal computer, a smartphone, a tablet device, or the like). The CPU 505, which is a control unit, receives these output data and command via the interface controller 501. The CPU 505 is an arithmetic processing unit that performs control of the entire compound introduction apparatus 100, such as receiving the output data, performing an introduction operation, conveying the ejection head, and so on. The CPU 505 analyzes the received command and, thereafter, loads and stores control signal data in the image memory 503, the control signal data being data for actuating the first heater 306 in the processing chamber 302, the second heater 307, which is a backflow preventing unit, and the third heater 308, which is a pressurization unit.

As an operation process to be performed before the compound introduction, the CPU 505 reads out the control signal data to be used in the introduction control from the image memory 503 in synchronization with conveyance of the ejection head 101. Then, the CPU 505 transfers this read data to the ejection head 101 via the ejection head control circuit 506. Moreover, the CPU 505 drives the first heater 306, the second heater 307, which is a backflow preventing unit, and the third heater 308, which is a pressurization unit, as needed to process a cell in the processing chamber 302 in the ejection head 101, so that the introduction-target compound is introduced into the cell. Thereafter, the CPU 505 causes the ejection head 101 to eject the cell suspension from the ejection port 305 toward the culture dish 107 from directly above the culture dish 107. Note that the control signal data may be stored in the work RAM 504, which is a work memory, instead of the image memory 503.

The operation of the CPU 505 is executed based on a processing program stored in the program ROM 502. The program ROM 502 stores the processing program, tables, and the like for the control process. The work RAM 504 or the like stores the time elapsed since the end of the last introduction process, and the CPU 505 executes commands of a capping process, an ejection port suction process, and the like according to the time elapsed. Also, the CPU 505 uses the work RAM 504 as a work memory.

The motor driving circuit 508 drives various motors such as a head up-down motor 509, the driving motor 102, a ventilation fan motor 510, a capping motor 511, the suction motor 105, and a stage conveyance motor 512.

<Introduction—Target Compound>

The compound to be introduced can be selected as appropriate according to its purpose. Conceivable examples of introducible compounds include nucleic acids, proteins, labeling substances, and the like. Note that the compound is not limited to these examples as long as it is a compound of such a size as to be containable within a cell into which it is to be introduced. However, in view of minimizing damage to the cells, the size of the compound is preferably ⅕ of the average diameter of the cells or smaller, and more preferably ⅒ of the average diameter of the cells or smaller.

The size of the cells can be measured by processing the cells with an enzyme or the like and then analyzing a cell suspension thus obtained with a laser diffraction particle size analyzer or the like. Alternatively, the size of the cells can be measured by placing the cell suspension on a hemacytometer or the like and observing it with an optical microscope. Moreover, the size of the compound to be introduced can also be measured in a similar manner. In particular, for a compound of a size of 1 μm or smaller, a dynamic light scattering particle size analyzer can be used. Representative compounds that can be employed in the present embodiment include nucleic acids.

<Nucleic Acids>

For the purpose of transient and stable expression of a nucleic acid or interference with a gene, an exogenous ribonucleic acid (RNA) or deoxyribonucleic acid (DNA) not different from ones derived from the compound introduction-target cells can be used as a compound to be introduced. As a nucleic acid higher-order structure, a single-stranded primary structure or a secondary structure, such as a hairpin-shaped stem-loop structure or a helix structure, can be used. Also, a tertiary structure, such as A-form, B-form, or Z-form, can be used. Also, a quaternary structure, such as a supercoiled shape, can be used. These higher-order structures can be preferably used according to the purpose. Also, these nucleic acids may be labeled with a fluorescent compound or a radioisotope, and any of these may be used according to the purpose.

<RNA>

RNAs to be handled in the present embodiment include messenger RNA, which is responsible for copying and carrying a sequence from DNA to the ribosome, which is a site where protein synthesis takes place. The RNAs also include ribosome RNA, which is a substance forming the ribosome, and transfer RNA, which carries amino acids of corresponding sequences to the ribosome. Others include small nuclear RNA, small nucleolar RNA, microRNA, and siRNA, which exhibits an interfering action, and the like. However, the RNAs are not limited to these, and a preferable RNA can be used according to the purpose.

<DNA>

As a DNA to be handled in the present embodiment, any of a single-stranded DNA, a double-stranded DNA, a triple-stranded DNA, and a four-stranded DNA can be selected. As its shape, a linear shape, a circular shape, or the like is generally used. In recent years, however, the shape is not limited and any shape can be used, as represented by DNA origami. A double-stranded DNA is preferable in view of substance stability, and a circular plasmid DNA is more preferable in view of ease of culture with *Escherichia coli* or yeast. Further, to be introduced into a cell, the DNA needs to be introduced into the cell from its cell membrane. For this reason, the surface area is preferably as small as possible. For example, in a case of DNAs with the same sequence, a circular one is more preferable than a stranded one, and a supercoiled DNA resulting from twisting of a DNA is more preferable.

<Proteins>

Proteins to be handled in the present embodiment include proteins and the like dissolved, dispersed, or dispersed in a state of being supported on a substrate in order to be introduced into the cell suspension. It suffices that their structure be a primary structure including an amino acid sequence and containing a polypeptide, a secondary structure such as α-helix or β-sheet, a tertiary structure including these secondary structures, and the quaternary structure of hemoglobin or the like, and higher-order structures corresponding to the purpose can be used. Specific examples include enzyme proteins such as amylase, structural proteins such as collagen and keratin, transport proteins such as albumin, storage proteins such as ferritin, and contractile proteins such as actin and myosin. The specific examples also include protective proteins such as globulin, modulated proteins such as calmodulin, as well as various membrane proteins, zinc-finger nuclease for genome editing, the Cas9 protein used in CRISPR/Cas9, and the like.

<Labeling Substance>

A labeling substance to be handled in the present embodiment only needs to be such that, in a state where it is introduced in a cell, a label is recognizable from outside the cell. Such a labeling substance may be introduced to any of the nucleic acids or proteins mentioned above via chemical or physical modification. It suffices that the absorption wavelength or luminous wavelength of the labeling substance be different from that of the compound introduction-target cell and be recognizable. Also, it suffices that the labeling substance be present in a dissolved state, a dispersed state, or a dispersed state in a state of being supported on a substrate in order to be introduced into the cell suspension. Specific examples include stable isotopic substances such as deuterium, C13, and N15, radioactive substances, dyes, fluorescent dyes, pigments, fluorescent pigments, quantum dots, nanodiamonds, fullerenes, carbon nanosheets, carbon nanotubes, and the like.

<Cell Types>

Cells to be handled in the present embodiment include adherent cells, suspension cells, spheroids (cell aggregates), and the like. Specific examples thereof include cells of human cervical cancer cell lines, neurons, hepatocytes, fibroblasts, myoblasts, smooth muscle cells, cardiac muscle cell, skeletal muscle cells, stem cells, mesodermal stem cells, embryonic stem cells, glial cells, fetal stem cells, and hematopoietic stem cells. The specific examples also include mast cells, adipocytes, neural stem cells, and blood cells, and the like.

Other examples include microbial cells and plant cells. More specifically, these include prokaryotes such as *Escherichia coli, Streptomyces, Bacillus subtilis, Streptococcus*, and *Staphylococcus*, eukaryotic cells such as yeast and *Aspergillus*, insect cells such as *Drosophila* S2 and *Spodoptera* Sf9, and the like. The average diameter of the cells is such that a cell can be ejected from an ejection port and is, for example, 1 or more and 100 μm or less.

<Cell Suspension>

The cell suspension has at least one introduction-target compound to be introduced and one or more cells into which the introduction-target compound is to be introduced and contains water as its main component. Further, in the present invention, the cell suspension is a liquid in which cells are dispersed. The cells in the cell suspension have only to be in a state in which the cells can be dispersed in the liquid by agitating, and may be precipitated in the liquid in a case where the cell suspension is kept in a stationary state. Incidentally, other components are preferably contained as appropriate so that the cells can survive during introduction processing and after it. These other components include salts, sugars, ribonucleotides, growth factor or hormone, pH buffer, surfactant, chelator, water-soluble organic solvent, proteins and amino acids, antibacterial agent, humectant, thickener, and the like.

<Salts>

Examples of the salts to be handled in the present embodiment only need to be inorganic or organic salts for use in cell culture. Specifically, they include sodium chloride, potassium chloride, sodium citrate, and the like.

<Sugars>

As examples of the sugars to be handled in the present embodiment, sugars as nutrient components for cells, sugars for adjusting the osmotic pressure, and the like can be used. Specifically, they include glucose, sucrose, fructose, and the like.

<Ribonucleotides>

As examples of the ribonucleotides to be handled in the present embodiment, ribonucleotides for assisting cellular metabolism can be used. Specifically, adenosine triphosphate, guanosine triphosphate, and the like.

<Growth Factor or Hormone>

Examples of the growth factor or hormone to be handled in the present embodiment include human growth hormones. The examples also include growth hormones of other animals (such as bovine, porcine, and chicken growth factors), insulin, oxytocin, angiotensin, methionine enkephalin, and substance P. The examples also include ET-1, FGF, KGF, EGF, IGF, PDGF, LHRH, GHRH, FSH, DDAVP, PTH, vasopressin, glucagon, somatostatin, and the like.

<pH Buffer>

Examples of the pH buffer to be handled in the present embodiment include a citrate buffer solution, a phosphate buffer solution, a Tris buffer solution, or a HEPES buffer solution, and the like.

<Surfactant>

Examples of the surfactant to be handled in the present embodiment include a water-soluble anionic surfactant, a water-soluble cationic surfactant, a water-soluble amphoteric surfactant, and a water-soluble nonionic surfactant, and one of these may be added or two or more may be added.

<Chelator>

Specific examples of the chelator to be handled in the present embodiment include ethylenediaminetetraacetic acid (EDTA), glycol ether diamine tetraacetic acid (EGTA), and the like.

<Water and Water-Soluble Organic Solvent>

The cell suspension to be handled in the present embodiment can use an aqueous liquid medium containing water or a mixture of water and a water-soluble organic solvent. The cell suspension can be obtained by adding the cells and the introduction-target compound to the aqueous liquid medium.

The solvent to be used in the present embodiment is not particularly limited, and examples thereof include water and saline. The examples also include a phosphate buffer solution (hereinafter PBS), a buffer solution of Tris or the like, and Dulbecco's Modified Eagle Medium (hereinafter D-MEM). The examples also include Iscove's Modified Dulbecco's Medium (hereinafter IMDM), Hanks' Balanced Salt Solutions (hereinafter HBSS), and the like. The examples also include Minimum Essential Medium-Eagle, Earle's Salts Base, with Non-Essential Amino Acid (hereinafter MEM-NEAA). The examples also include culture solutions for cell culture such as Roswell Park Memorial Institute Medium (RPMI) 1640 and the like. The examples also include commercially available buffers for electroporation, commercially available buffers for FACS analysis, and the like, as well as infusion solutions such as lactated Ringer's solution. It is particularly preferable that these solvents contain 50% water or more. Also, two or more of these solvents can be mixed and used. The water is preferably water deionized by ion exchange or the like and sterilized by heating with an autoclave or the like. Also, the content of water in the cell suspension medium is preferably 30% by mass or more and 99% by mass or less relative to the mass of the cell suspension.

The water-soluble organic solvent is not limited to a particular kind, and any publicly known organic solvent can be used according to the purpose. Specific examples include glycerin, polyethylene glycol, dimethyl sulfoxide, and the like. The content of the water-soluble organic solvent in the cell suspension is preferably 0.001% by mass or more and 50% by mass or less relative to the entire mass of the cell suspension.

<Proteins and Amino Acids>

Examples of the proteins and amino acids to be handled in the present embodiment include serums such as fetal bovine serum (hereinafter FBS) and horse serum.

<Antibacterial Agent>

Examples of the antibacterial agent to be handled in the present embodiment include antibiotics such as sodium azide and penicillin-streptomycin, and each can be used by adding it to the cell suspension. In particular, saline, PBS or a buffer solution of Tris or the like, a culture medium for cell culture such as D-MEM, IMDM, or HBSS, a commercially available buffer for FACS analysis, or the like, an infusion solution such as lactated Ringer's solution, or the like is preferably used for controlling the salinity, pH, or the like suitable for the cells.

<Humectant>

Examples of the humectant to be handled in the present embodiment include polyalcohols such as glycerin, propylene glycol, butylene glycol, and sorbit. The examples also include mucopolysaccharides such as hyaluronic acid and chondroitin sulfate, hydrolyzed proteins soluble collagen, elastin, and keratin, and the like. One of these may be used alone or two or more may be mixed and used.

<Thickener>

Examples to the thickeners to be handled in the present embodiment include starches such as an oxidatively modified starch, an enzymatically modified starch, a thermochemically modified starch, a cationic starch, an amphoteric starch, and an esterified starch. The examples also include cellulose derivatives such as carboxymethyl cellulose, hydroxyethyl cellulose, and ethyl cellulose, and natural or semisynthetic polymers such as casein, gelatin, or soybean protein. The examples also include completely or partially saponified water-soluble polymeric compounds. The water-soluble polymeric compounds include polyvinyl alcohol, acetoacetylated polyvinyl alcohol, and carboxy-modified polyvinyl alcohol. The examples also include polyvinyl alcohols such as olefin-modified polyvinyl alcohol and silyl-modified polyvinyl alcohol. At least one water-soluble polymeric compound can be selected from among these as appropriate and used. In the present embodiment, the viscosity of the liquid to be used is preferably 0.1 pascal-second (Pa·s) or more, and any of the above thickeners may be added as needed.

<Compound Introduction Method>

In a compound introduction method in the present embodiment, cells cultured by adherent culture, suspension culture, or the like are separated into single cells or small cell aggregates via an action of an enzyme or the like and then, with a centrifuge or the like, only the cells are caused to settle by utilizing the difference in relative density. Thereafter, the supernatant medium excluding the cells is removed, and then the medium containing the introduction-target compound is added followed by agitation with a pipette or an agitator. As a result, a cell suspension is prepared.

The concentration of the cell suspension to be prepared may be adjusted according to the purpose and, is, in view of production efficiency, preferably 1000 cells/mL or more and 100000000 cells/mL or less and more preferably 100000 cells/mL or more and 10000000 cells/mL or less.

Incidentally, it is preferable that, before the introduction of the cell suspension into the ejection head 101 to be used, the cell suspension be passed through a cell strainer having substantially the same diameter as the smallest diameter of the flow channels in the ejection head. In this way, large cell aggregates can be excluded from the cell suspension. The cell suspension thus prepared is introduced into the ejection head 101 by using a micropipette or the like. In a case where the cell suspension is smoothly filled to the ejection ports 305 of the ejection head 101 with wetting and spreading of the cell suspension due to surface tension, the introduction operation is executed as soon as the cell suspension is filled. In a case where the cell suspension cannot be filled to the ejection ports 305 of the ejection head 101, the cell suspension can be filled via suction from the ejection ports 305 with the suction mechanism 104 or an external suction pump. Alternatively, the cell suspension can be filled by pressurizing the reservoir part 201 holding the cell suspension therein with an external pressurization pump.

The cell suspension to be ejected is ejected to a base material or culture solution. The base material needs to be selected with the total load to be received by the cells taken into account, and is selected according to the purpose. Specifically, in a case of performing introduction processing by ejection onto a base material, it is preferable to immerse the cells in a culture medium containing a serum or an extracellular matrix or the like in advance and eject the cell suspension thus processed if the base material is an adherent base material whose surface has high affinity to the cells, such as glass or polystyrene. Also, in a case of using a fluororesin having low affinity to the cells, such as PTFE, or the like as the base material, it is preferable to transfer the ejection-target liquid into a culture medium after it is ejected. In a case of executing an introduction operation on a culture dish, it is preferable to bring the cells into contact with a culture medium containing a serum or an extracellular matrix on the culture dish in advance. It is also possible to directly eject the cells from the ejection head 101 onto a culture medium filled in a culture dish. The method is selected according to the purpose.

While the cell suspension can be transferred to a dish containing a culture medium that is optimal for the cells immediately after the ejection, the cell suspension can also be kept under a saturated aqueous vapor environment. In a case of increasing the amount to be introduced, it is preferable to let the cell suspension stand.

In the case of ejecting the cells onto a base material, a method involving removing the cell culture solution on the base material with a pipette or the like and seeding the cells onto a dish may be employed. In this case, it is possible to put the whole base material in the dish, add a culture medium, and culture the cells therein. Further, once the cell suspension is ejected, it may be introduced into the ejection head 101 and ejected therefrom again. In this way, a compound introduction operation can be repeated. In this case, it is preferable to use a base material whose surface has low affinity to the cells.

<Method of Culture Operation>

The cells processed can be cultured in an intended culture system. Specifically, in a case of animal cells, the cells are preferably cultured in an incubator in which is kept a saturated aqueous vapor at a culture temperature of 37 degrees Celsius and a carbon dioxide concentration of 5%. During the culture, it is preferable to check the cell's state of growth and replace the culture medium or perform passaging.

<Method of Checking Introduction of Compound into Cells>

The method of checking the introduction of the compound into the cells varies depending on the compound to be introduced. Thus, a suitable checking method may be used as appropriate. For example, in a case where a plasmid DNA that expresses GFP, which is a fluorescent protein, is introduced into the cells, a sample after the elapse of a certain time may be checked with a fluorescence microscope as to whether light is emitted from GFP. In this way, the amount to be introduced can be checked semiquantitatively. Also, the cultured cells may be separated into single cells by using an enzyme or the like and then the number of light-emitting cells may be counted by flow cytometry. In this way, the introduction can be checked quantitatively. Further, the cells can be dissociated and measured using a fluorescence spectrophotometer, a luminometer, or the like. Moreover, it is possible to use ELISA or immunostaining using antigen-antibody reaction. It is also possible to measure the introduced DNA and amplified DNA in the cells by using a real-time PCR apparatus or the like. In a case where the introduced compound is a labeling compound, an analysis can be made using an analysis unit for use in common chemical analyses.

<Thermal Action of Heater in Processing Chamber>

The thermal action of the heater in the processing chamber 302 brings about an effect of promoting expression of a heat shock protein gene in the cell or a gene that promotes cell division, as described by Campbell et al. in "Campbell, A et al., 2020 Frontiers in Bioengineering and Biotechnology, 8 doi: 10.3389/fbioe.2020.00082". Owing to this effect, the technique of the present embodiment is effective in a case of introducing a nucleic acid into a dividing cell to modify genes in the cell.

Example

An example in the present embodiment will be described below. Note that the following example is a mere instance, and the present embodiment is not limited to this instance. "Parts" and "%" in some sentences are based on mass unless otherwise noted.

Firstly, the ejection head 101 was washed with a plenty of sterile water. Further, in a biological clean bench, the inside and outside of the ejection head 101 were cleaned and disinfected using an aqueous solution containing 70 parts ethanol. After removing an excess portion of the ethanol aqueous solution, the inside and outside of the ejection head 101 were washed using 15 mL of a 1×phosphate-buffered saline (1×PBS) (manufactured by Thermo Fisher Scientific K.K., pH=7.4). Further, 5 mL of 1×PBS was additionally introduced into the reservoir part 201 of the ejection head 101. In this state, the 1×PBS was sucked out from the ejection port surface of the ejection head in a communicating state by using an external aspirator connected to a sterilized tube. This operation was performed three times. As a result, the ejection head 101 sterilized was obtained.

The cell suspension and the introduction-target compound used in the compound introduction apparatus 100 in FIG. 1 were prepared as below.

As the introduction-target compound, a DNA solution containing DNA was prepared as below.

First, 0.2 mL of 0.5 mol/L-EDTA Solution (pH 8.0) (manufactured by NACALAI TESQUE, INC.) and 1 mL of 1 mol/L-Tris-HCl Buffer Solution (pH 8.0) (manufactured by NACALAI TESQUE, INC.) were mixed to thereby obtain a mixed liquid.

Next, 98.8 mL of sterilized pure water was added to this mixed liquid to thereby prepare a TE buffer (10 mM Tris 1 mM EDTA (pH 8)). Freeze-dried CMV-Fresno RFP (manufactured by ATUM, the number of base pairs=5.5 kbp) and the prepared TE buffer were mixed and agitated in a microtube, and the DNA was dissolved in that mixture. As a result, a DNA solution was obtained. Part of the obtained DNA solution was further diluted with the TE buffer and then filled into a quartz cell. Thereafter, with a DNA concentration measurement apparatus (GeneQuant 1300, manufactured by Biochrom), concentration identification was performed to thereby figure out the concentration of the DNA solution. The DNA concentration was 2.0 μg/μL.

The cell suspension was prepared through the following procedure.

RAW 264.7 purchased from the American Type Culture Collection, which was a cell line established from murine monocytic leukemia, was subjected to the following procedure so as to increase to 2000000 cells/mL.

The cell line, or RAW 264.7, was dispersed in 20 mL of a D-MEM culture medium containing 10% FBS, 1% penicillin-streptomycin, and 1% MEM-NEAA so as to increase to 2000000 cells/mL. Thereafter, groups of approximately 1000000 cells were seeded on a 100-mm polystyrene dish.

As the 10% FBS, one manufactured by Global Life Science Technologies Japan K.K. was used. As the 1% penicillin-streptomycin, one manufactured by Sigma-Aldrich Co. LLC. was used. As the 1% MEM-NEAA, one manufactured by Thermo Fisher Scientific K.K. was used. As the D-MEM, one manufactured by Thermo Fisher Scientific K.K. was used. As the 100-mm polystyrene dish, one manufactured by Corning Incorporated was used.

A dish having the D-MEM culture medium containing the seeded cells was incubated at 37° C. in the presence of 5% $CO_2$ to thereby amplify the cells. After two to four days, a state where the cells covered approximately 70% of the bottom surface of the dish was confirmed. Then, the supernatant culture medium was removed, followed by rinsing with PBS. The cells were detached from the dish by using PBS containing 0.25% trypsin and 1 mM EDTA (manufactured by Thermo Fisher Scientific K.K.). Thereafter, the cell suspension containing the RAW 264.7 cells was collected from the dish.

Inside a sterilized centrifuge tube, the above-mentioned D-MEM culture medium was added to the cell suspension collected from the dish such that the total amount would be 50 mL, followed by processing with a centrifuge (CF16RX II, manufactured by Hitachi, Ltd.) set at a centrifugal force of 90 G at a temperature of 4 degrees Celsius for five minutes to thereby cause the cells to settle. The supernatant over the settled cell pellet was quietly removed, and then the above-mentioned D-MEM culture medium was added to the cell pellet. As a result, a cell suspension was obtained. This cell suspension was subjected to the above-described cell culture operation again twice.

In the third operation, a number of cells necessary to achieve a desired cell concentration were taken into another separate centrifuge tube. Then, after centrifugation, a liquid composition prepared by mixing equal amounts of the DNA solution and Gene Pulser electroporation buffer (manufactured by Lonza K.K.) was added instead of the above-mentioned D-MEM culture medium, followed by agitation with a micropipette. Further, the resultant liquid was passed through a cell strainer (manufactured by Corning Incorporated, mesh size=40 μm). As a result, a cell suspension to be used in the introduction of the compound into the cells was obtained.

In this example, the compound introduction apparatus 100 in FIG. 1 was used to introduce the DNA into the cells as below.

First, 200 μL of the cell suspension prepared by the above-described operations was introduced into the ejection head 101 by using a micropipetter. Thereafter, the ejection head 101 was conveyed to and brought into contact with the suction mechanism 104 and then the suction motor 105 was actuated, so that the cell suspension was filled into the flow channels and the ejection ports 305 in the ejection head 101. After the filling, an introduction operation program was executed. As a result of executing the introduction operation program, the ejection head 101 was separated from the suction mechanism 104 and conveyed to above a glass bottom dish (manufactured by Iwaki) set in advance whose inner bottom surface was wetted by 100 μL of the above-described D-MEM culture medium, and the cell suspension was ejected into the glass bottom dish. As a result, a sample was obtained.

The sample thus obtained was covered with the glass bottom dish's top plate and taken out of the apparatus. Thereafter, 2.5 mL of the above-described D-MEM culture medium warmed up to 37° C. was quietly poured using a micropipette, followed by incubation at 37° C. in the presence of 5% $CO_2$, so that the cells were amplified. 24 hours later, the gene introduction rate (DNA introduction rate) was evaluated using a fluorescence microscope.

The CMV-Fresno RFP used in this example contains a gene that generates a protein which emits red fluorescence in a case where it is introduced into a cell. Thus, expression of this fluorescent protein was utilized to evaluate the gene introduction rate.

The gene introduction rate was evaluated through the following procedure.

The gene introduction rate of the cells subjected to the above-described DNA introduction was measured. Specifically, from the sample after the 24-hour incubation, the culture medium was removed, followed rinsing with 1×PBS and addition of 2 mL of 1×PBS. After the culture medium was replaced with 1×PBS, the sample was observed using a fluorescence microscope (manufactured by Keyence Corporation, model number: BZ-8000). The observation was performed with a 10× object lens in a bright-field mode and a fluorescence mode (TRITC: excitation=540±12.5 nm, fluorescence=605±27.5 nm, cut=565 nm). Then, whether a fluorescent protein was expressed in the cells by the DNA introduction was checked by counting the number of fluorescence-emitting cells and the number of all cells, and (Number of Fluorescence-Emitting Cells/Number of All Cells)×100 was calculated to derive the gene introduction rate. As a result, the gene introduction rate was 5% or more.

Meanwhile, the present inventors considered modeling an ejection head without the second heater 307, which was a backflow preventing unit, and the third heater 308, which was a pressurization unit configured to apply a pressure to the discharge flow channel, as a comparative example similar to the conventional technique. Moreover, the present inventors considered a case as a comparative example where the second heater 307, which was a backflow preventing unit, and the third heater 308, which was a pressurization unit, were controlled not to be driven. In this case, the cell suspension was not ejected from the ejection port unless the first heater 306 in the processing chamber 302 was brought into a film boiling state. The gene introduction rate into the cells in this case of control was approximately 1%.

Second Embodiment

In a second embodiment, a description will be given of an example which differs from the first embodiment in the configuration of the backflow preventing unit in the ejection head 101 described in the first embodiment.

Figure 6:
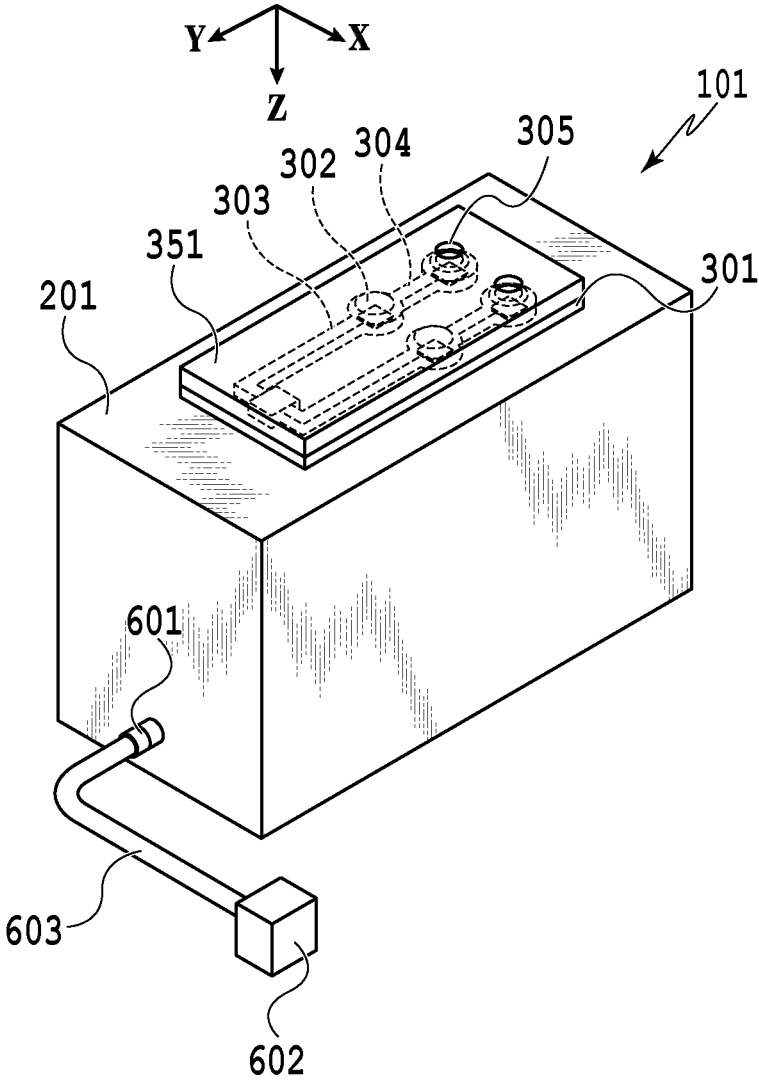
FIG. 6 is a perspective view of an ejection head.

FIG. 6 is a perspective view of the ejection head 101 in the present embodiment. The backflow preventing unit in the present embodiment is a liquid feed mechanism 602 that feeds a cell suspension. In the present embodiment, a supply port 601 for supplying the cell suspension or air into the reservoir part 201 of the ejection head 101 is formed, for example. The supply port 601 and the liquid feed mechanism 602 communicate with each other through a tube 603. In the present embodiment, the cell suspension filled in the reservoir part 201 is pressurized from the liquid feed mechanism 602 to thereby be supplied into each supply flow channel 303. In this supply control, the cell suspension may be continuously pressurized from the liquid feed mechanism 602, or the mechanism may be intermittently driven in synchronization with each third heater 308, which is a pressurization unit configured to pressurize the corresponding discharge flow channel 304, and the first heater 306 in each processing chamber 302. In the case of intermittently driving the liquid feed mechanism 602, as mentioned in the first embodiment, one of the liquid feed mechanism 602 or the third heater 308 in the discharge flow channel 304, which is a pressurization unit, may be driven first, and the other may be driven while the pressure is positive relative to the state before the start of the pressurization.

Note that the pressure to be applied by the liquid feed mechanism 602 to pressurize the cell suspension is preferably set such that the pressure in the supply flow channel 303 and the pressure in the discharge flow channel 304 are substantially in equilibrium and flow of the cell suspension in the processing chamber 302 can be prevented. Moreover, the pressure to be applied by the liquid feed mechanism 602 to pressurize the cell suspension is preferably set by taking into account the bubble generation pressure of the third heater 308, which is a pressurization unit configured to pressurize the discharge flow channel 304.

Figure 7A:
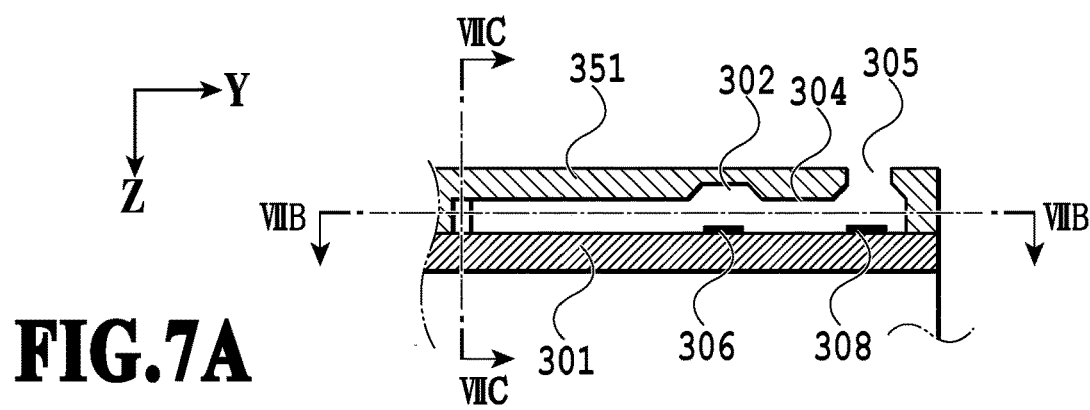
FIGS. 7A to 7C are views illustrating an example of the positional relationship among components formed on an electronic substrate.
Figure 7B:
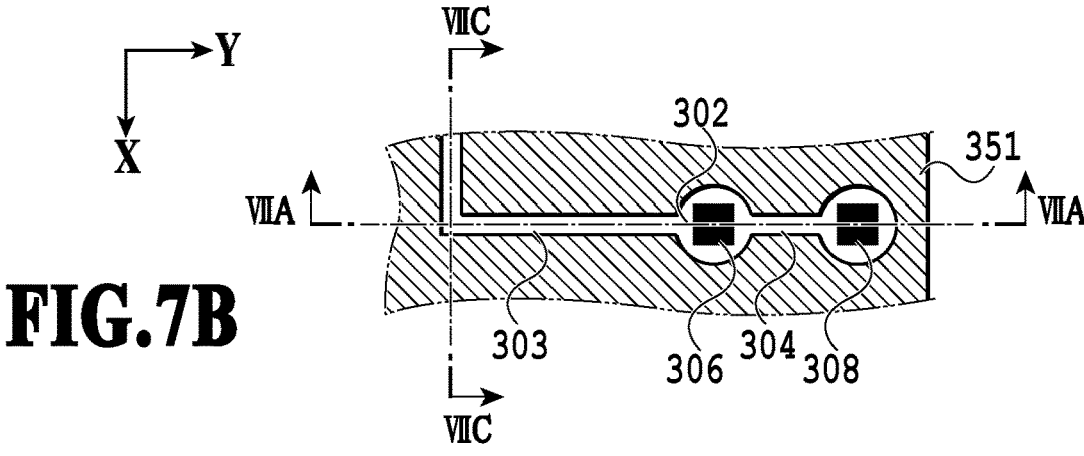
Figure 7C:
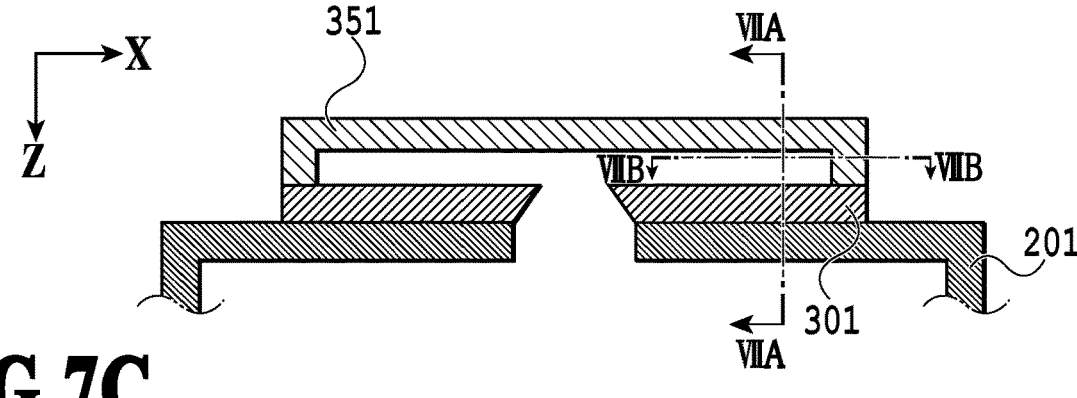

FIGS. 7A to 7C are views illustrating an example of the positional relationship among components formed on the electronic substrate 301 in the present embodiment. FIG. 7A is a vertical cross-sectional view along line VIIa in FIGS. 7B and 7C. FIG. 7B is a horizontal cross-sectional view along line VIIb in FIGS. 7A and 7C. FIG. 7C is a vertical cross-sectional view along line VIIc in FIGS. 7A and 7B. As illustrated in FIGS. 7A to 7C, in the present embodiment, the second heater 307 described in the first embodiment is not arranged on the electronic substrate 301. Moreover, the bubble generation chamber corresponding to the second heater 307 is not arranged either.

In order to check the effect of the present embodiment, the present inventors verified the effect by a method in which the cell suspension was continuously supplied to the reservoir part 201 by using a liquid feed pump as the liquid feed mechanism 602 to supply the cell suspension to the supply flow channel while slightly pressurizing the cell suspension. First, to figure out the supply conditions for the liquid feed mechanism 602, the amount of the cell suspension supplied by the liquid feed mechanism 602 was adjusted while the third heater 308, which was a pressurization unit configured to pressurize the discharge flow channel 304, was intermittently driven. Also, the present inventors found conditions with which the flow of the cell suspension in the flow channel including the processing chamber 302 temporarily stopped while the third heater 308 was driven, and then the flow restarted as the third heater 308 finished being driven, and adjusted the driving conditions for the liquid feed mechanism 602. The gene introduction rate in the present embodiment described above was evaluated by a method similar to the method mentioned in the description of the first embodiment. As a result, the introduction rate was 5% or more.

Note that, in the present embodiment, the third heater 308, which is a pressurization unit, preferably pressurizes the discharge flow channel 304 as soon as the ejection port 305 is refilled with the cell suspension. This can lower the probability of cells passing the processing chamber 302 without being processed.

Note that, in the present embodiment, an example has been shown in which the second heater 307 described in the first embodiment and the bubble generation chamber corresponding to the second heater 307 are not arranged on the electronic substrate 301. However, these may be arranged on the electronic substrate 301. Moreover, the second heater 307 may be controlled not to be driven or controlled to generate a bubble with the pressurization by the liquid feed mechanism 602 and the bubble generation pressure of the third heater 308 taken into account.

Third Embodiment

In a third embodiment, a description will be given of an example which differs from the second embodiment in the configuration of the pressurization unit in the ejection head 101 described in the second embodiment. Moreover, the configuration of the reservoir part 201 also differs from the second embodiment.

Figure 8A:
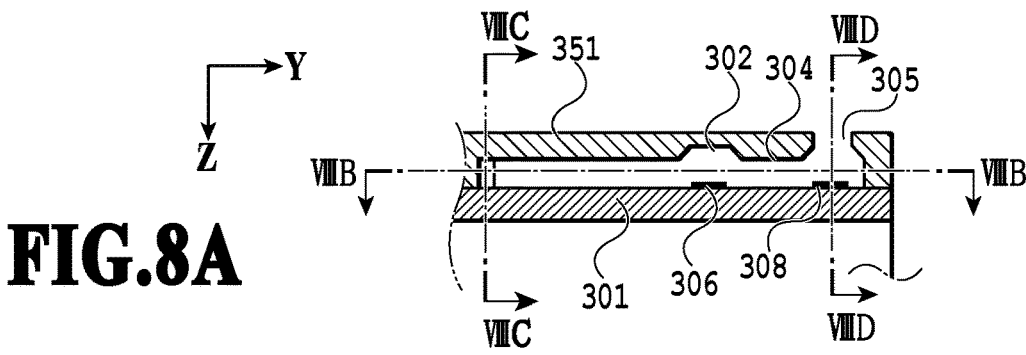
FIGS. 8A to 8D are views illustrating an example of the positional relationship among components formed on an electronic substrate.
Figure 8B:
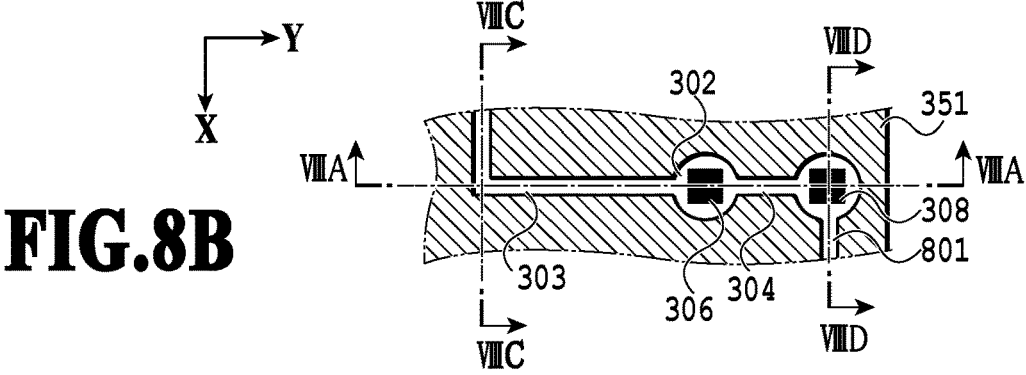
Figure 8C:
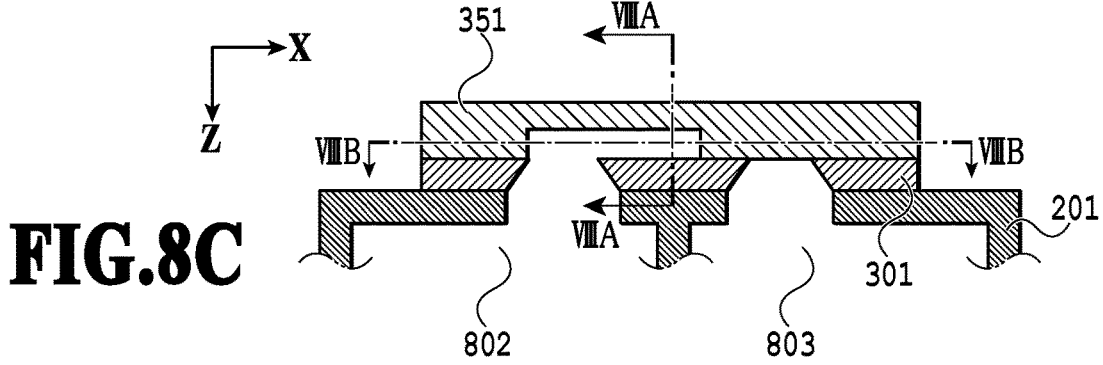
Figure 8D:
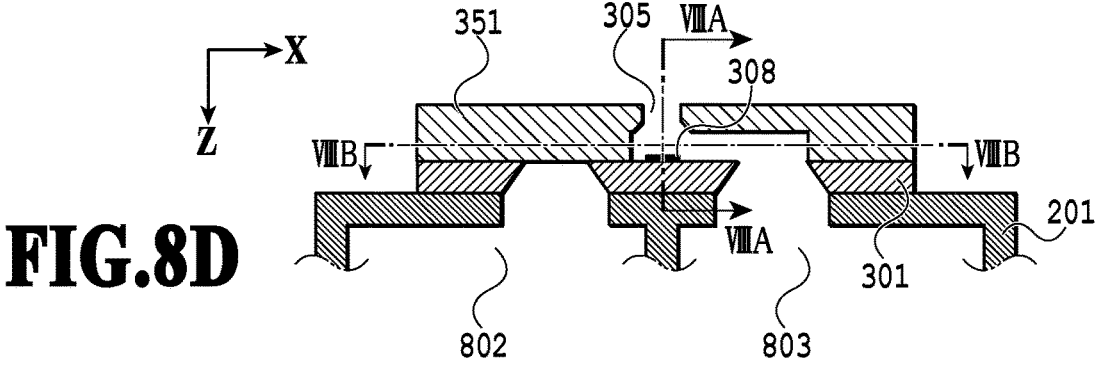

FIGS. 8A to 8D are views illustrating an example of the positional relationship among components formed on the electronic substrate 301 in the present embodiment. FIG. 8A is a vertical cross-sectional view along line VIIIa in FIGS. 8B, 8C, and 8D. FIG. 8B is a horizontal cross-sectional view along line VIIIb in FIGS. 8A, 8C, and 8D. FIG. 8C is a vertical cross-sectional view along line VIIIc in FIGS. 8A, 8B, and 8D. FIG. 8D is a vertical cross-sectional view along line VIIId in FIGS. 8A, 8B, and 8C.

In the present embodiment, in addition to the third heater 308, a pressurization flow channel 801 is included as a unit configured to pressurize the discharge flow channel 304. The pressurization flow channel 801 is a separate flow channel from the flow channels communicating with the processing chamber 302. The reservoir part 201 includes therein a first liquid chamber 802 communicating with the supply flow channel 303 and a second liquid chamber 803 communicating with the pressurization flow channel 801. The second liquid chamber 803 is provided with a liquid feed mechanism not illustrated, which pressurizes the second liquid chamber 803 in a similar manner to that described in the second embodiment to supply a liquid therein to the pressurization flow channel 801. As a result, the inside of the discharge flow channel 304 is pressurized by the liquid supplied from the pressurization flow channel 801.

Note that a cell suspension may be held in both the first liquid chamber 802 and the second liquid chamber 803, or a liquid containing no cell may be held in the second liquid chamber 803. For example, as illustrated in FIG. 8B, the pressurization flow channel 801 may be provided near the ejection port 305, and the liquid containing no cell may be supplied from the pressurization flow channel 801. In this way, it is possible to appropriately recover from a state where a cell is stuck in the ejection port 305.

Note that, in the present embodiment, an example has been described in which the backflow preventing unit described in the second embodiment is included. However, the backflow preventing unit described in the first embodiment may be included. That is, a configuration in which the second heater 307 is included in the supply flow channel 303 may be employed.

Fourth Embodiment

In a fourth embodiment, a description will be given of an example which differs from the first embodiment in the configuration of the backflow preventing unit in the ejection head 101 described in the first embodiment.

Figure 9A:
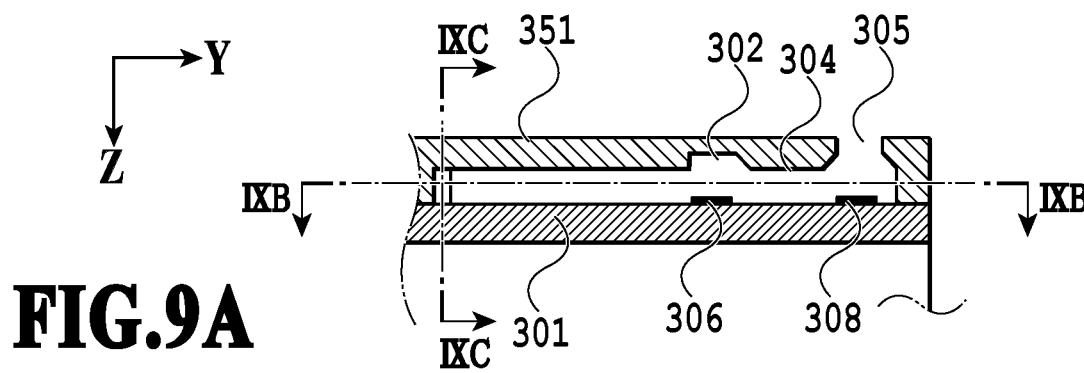
FIGS. 9A to 9C are views illustrating an example of the positional relationship among components formed on an electronic substrate.
Figure 9B:
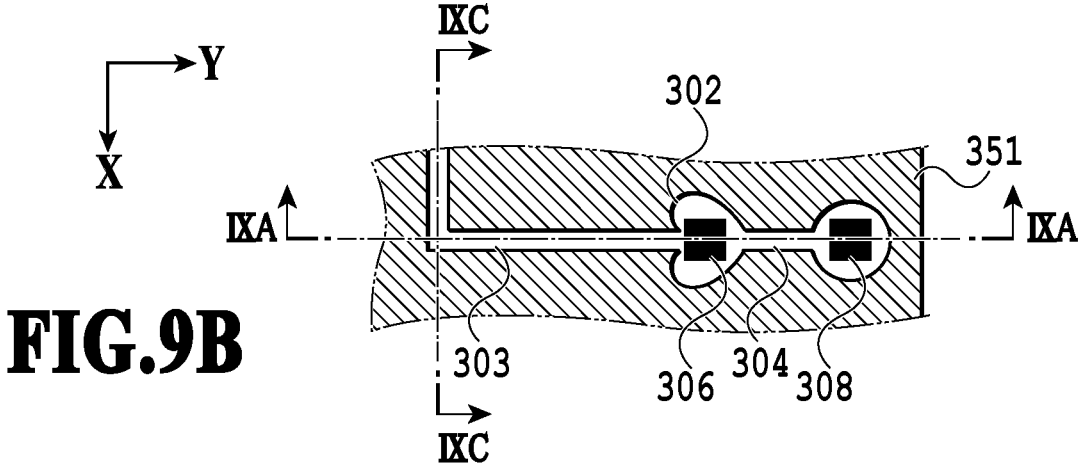
Figure 9C:
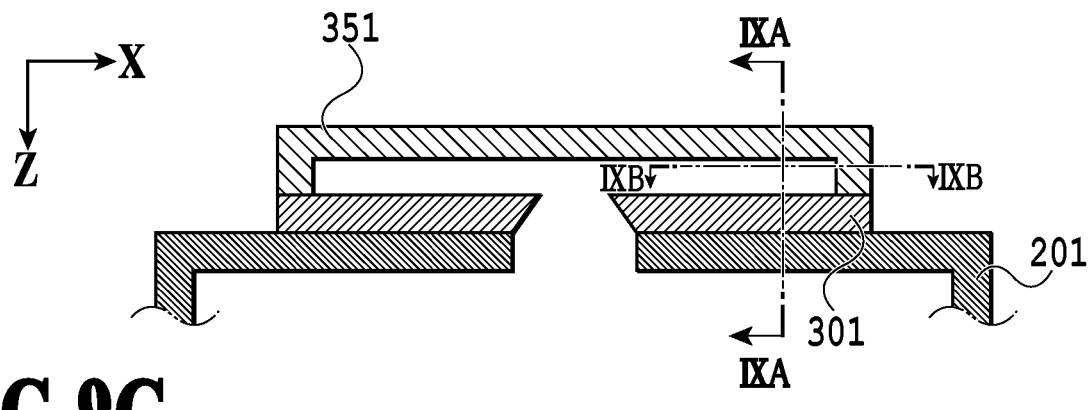

FIGS. 9A to 9C are views illustrating an example of the positional relationship among components formed on the electronic substrate 301 in the present embodiment. FIG. 9A is a vertical cross-sectional view along line IXa in FIGS. 9B and 9C. FIG. 9B is a horizontal cross-sectional view along line IXb in FIGS. 9A and 9C. FIG. 9C is a vertical cross-sectional view along line IXc in FIGS. 9A and 9B. As illustrated in FIGS. 9A to 9C, in the present embodiment, the second heater 307 is not arranged on the electronic substrate 301. Moreover, the bubble generation chamber corresponding to the second heater 307 is not arranged either.

As illustrated in FIG. 9B, in the present embodiment, the shape of the processing chamber 302 is a shape having the function of a check valve as a backflow preventing unit configured to prevent backflow of a cell suspension from inside the processing chamber 302 into the supply flow channel 303. FIG. 9B illustrates an example in which the shape of the processing chamber 302 is a heart shape, for example, in order to achieve the effect of a check valve. More specifically, in a plan view of the processing chamber 302, its shape is such that an upper portion of the heart (the portion where the two arcs join) is connected to the supply flow channel 303. Providing the processing chamber 302 of such a shape can lower the probability of cells contained in the cell suspension flowing back to the supply flow channel 303 side after flowing into the processing chamber 302 from the supply flow channel 303. Thus, in a case where the cell suspension in the processing chamber 302 attempts to flow back to the supply flow channel 303 side due to a flow generated as a result of driving the third heater 308, which is a pressurization unit, the cell in the processing chamber 302 is more likely to remain in it. This can raise the probability of the compound being introduced into the cell in the processing chamber 302.

Note that the configuration in the present embodiment may be combined to any one of the first to third embodiments. For example, the present embodiment and the first or second embodiment may be combined. This can further prevent backflow of the cell suspension. The combination can also widen the allowable pressure difference range within which the pressure to be generated on the supply flow channel 303 side and the pressure to be generated on the discharge flow channel 304 side for preventing flow of the cell suspension in the processing chamber 302 to temporarily trap the cell in the processing chamber 302 counterbalance each other. This also allows for an improvement in the degree of freedom in the design of the ejection head 101.

Fifth Embodiment

In a fifth embodiment, a description will be given of an example which differs from the first embodiment in the configuration of the backflow preventing unit in the ejection head 101 described in the first embodiment.

Figure 10A:
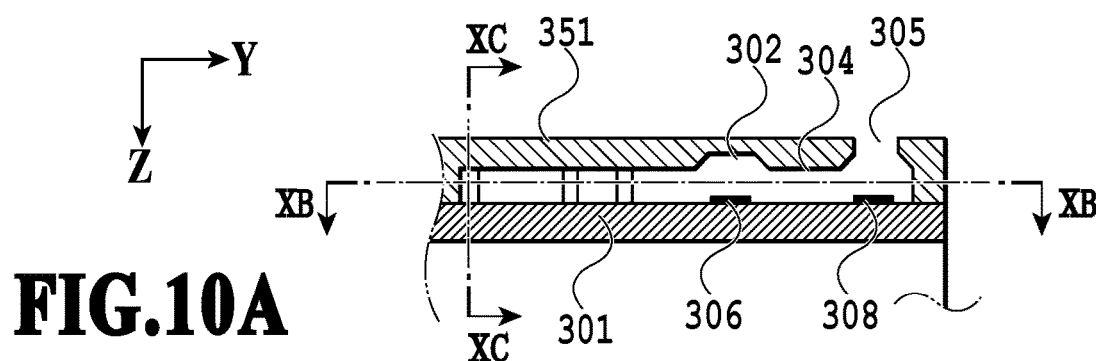
FIGS. 10A to 10C are views illustrating an example of the positional relationship among components formed on an electronic substrate.
Figure 10B:
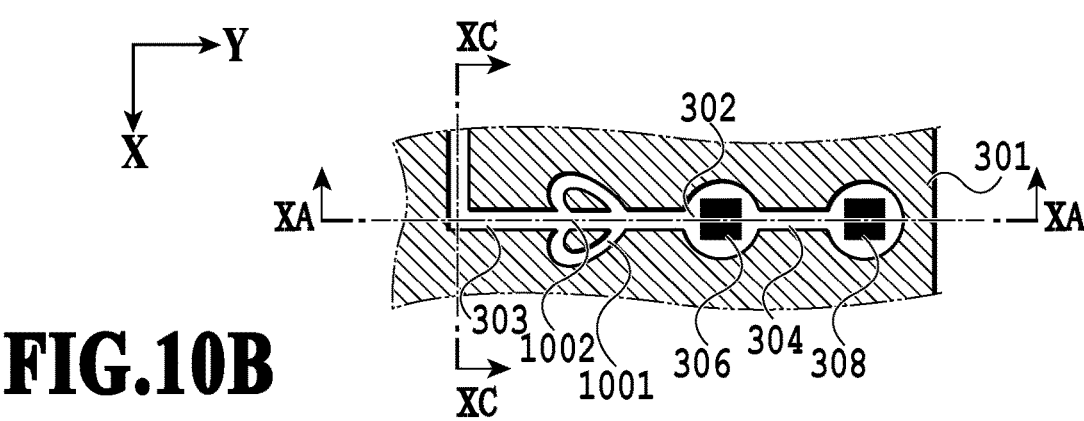
Figure 10C:
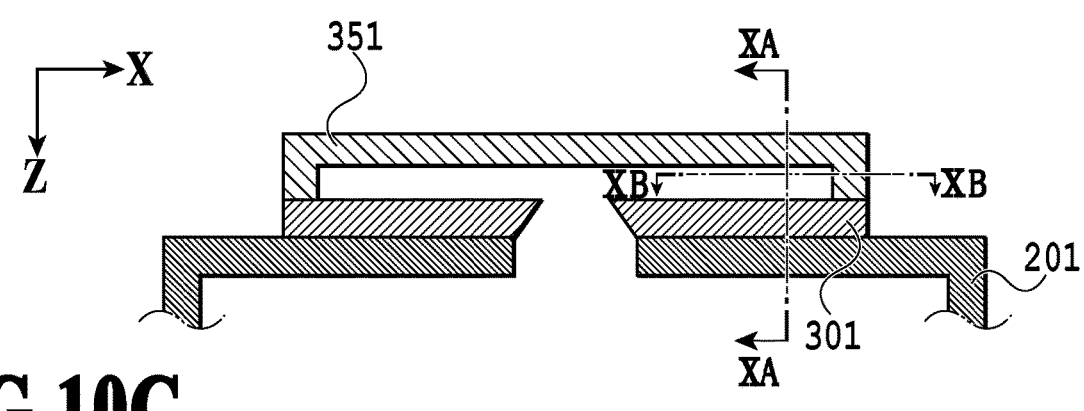

FIGS. 10A to 10C are views illustrating an example of the positional relationship among components formed on the electronic substrate 301 in the present embodiment. FIG. 10A is a vertical cross-sectional view along line Xa in FIGS. 10B and 10C. FIG. 10B is a horizontal cross-sectional view along line Xb in FIGS. 10A and 10C. FIG. 10C is a vertical cross-sectional view along line Xc in FIGS. 10A and 10B. As illustrated in FIGS. 10A to 10C, in the present embodiment, the second heater 307 is not arranged on the electronic substrate 301.

In the present embodiment, as illustrated in FIG. 10B, the shape of the supply flow channel is a shape having the function of a check valve as a backflow preventing unit configured to prevent backflow of a cell suspension from the processing chamber 302 into the supply flow channel. Specifically, a supply flow channel 1002 in the present embodiment is such that a flow channel which serves as a so-called fluid diode is formed in the supply flow channel, in order to achieve the effect of a check valve.

By using a shape as described above, in a case where a cell contained in the cell suspension attempts to flow back to the supply flow channel 1002 side after flowing into the processing chamber 302 from the supply flow channel 1002, bypass flow channels 1001 can prevent the backflow. Specifically, a shape as described above functions such that the backward flow passing through the bypass flow channels 1001 returns to the supply flow channel 1002 in the fluid diode to become a forward flow. This can lower the probability of the cell suspension flowing back to the supply flow channel 1002 side from the processing chamber 302. Thus, as with the example described in the fourth embodiment, it is possible to raise the probability of the compound being introduced into the cell in the processing chamber 302.

Note that a configuration combining the present embodiment and any one of the first to fourth embodiments may be employed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2021-044715, filed Mar. 18, 2021, and No. 2022-037270, filed Mar. 10, 2022, which are hereby incorporated by reference wherein in their entirety.

What is claimed is:

1. A compound introduction apparatus for introducing a compound into a cell, comprising:

a processing chamber;

an introduction unit configured to introduce the compound into the cell inside the processing chamber;

a supply flow channel for supplying a cell suspension containing the cell and the compound to the processing chamber;

a discharge flow channel for discharging the cell suspension from the processing chamber;

a backflow preventing unit configured to prevent backflow of the cell suspension from the processing chamber into the supply flow channel; and a pressurization unit configured to pressurize the discharge flow channel, wherein the backflow preventing unit, the introduction unit, and the pressurization unit are arranged in this order from a supply side of the cell suspension, wherein the introduction unit has a first energy generation element that generates energy, wherein the backflow preventing unit has at least one selected from the group consisting of a second energy generation element that generates energy, a liquid feed mechanism that supplies the cell suspension, and a check valve, and wherein the pressurization unit has a third energy generation element that generates energy.

2. The compound introduction apparatus according to claim 1, wherein the first energy generation element is a first heater.

3. The compound introduction apparatus according to claim 1, wherein the backflow preventing unit has the second energy generation element that is arranged in the supply flow channel.

4. The compound introduction apparatus according to claim 3, wherein the second energy generation element arranged in the supply flow channel is a second heater.

5. The compound introduction apparatus according to claim 1, wherein the backflow preventing unit has the liquid feed mechanism that supplies the cell suspension to the supply flow channel.

6. The compound introduction apparatus according to claim 1, wherein the check valve has a heart shape.

7. The compound introduction apparatus according to claim 1, wherein the backflow preventing unit has the check valve provided in the supply flow channel.

8. The compound introduction apparatus according to claim 1, wherein the shape of the check valve is a shape including a bypass flow channel through which a backward flow returns to a forward flow.

9. The compound introduction apparatus according to claim 1, wherein the pressurization unit has the third energy generation element that is arranged in the discharge flow channel.

10. The compound introduction apparatus according to claim 9, wherein the third energy generation element arranged in the discharge flow channel is a third heater.

11. The compound introduction apparatus according to claim 1, wherein the pressurization unit has a pressurization flow channel which communicates with the discharge flow channel and to which a pressurized liquid is supplied.

12. The compound introduction apparatus according to claim 1, wherein the introduction unit is driven in a state where a pressure has been applied by the pressurization unit to an inside of the discharge flow channel and a pressure inside the discharge flow channel is higher than the pressure before the pressure application.

13. The compound introduction apparatus according to claim 1, wherein the introduction unit is driven in a state where a pressure has been applied by the backflow preventing unit to an inside of the supply flow channel and a pressure inside the supply flow channel is higher than the pressure before the pressure application.

14. The compound introduction apparatus according to claim 4, wherein the first energy generation element is a first heater, and an amount of electric power to be applied to the second heater is larger than an amount of electric power to be applied to the first heater.

15. The compound introduction apparatus according to claim 9, wherein the first energy generation element is a first heater, and an amount of electric power to be applied to the third heater is larger than an amount of electric power to be applied to the first heater.

* * * * *